US010555956B2

(12) United States Patent
Grande et al.

(10) Patent No.: US 10,555,956 B2
(45) Date of Patent: Feb. 11, 2020

(54) CHEMOPREVENTION OF COLORECTAL CANCER

(71) Applicant: SOFAR SPA, Trezzano Rosa (MI) (IT)

(72) Inventors: Alexis Grande, Modena (IT); Fabrizio Ferrarini, Modena (IT); Sandra Parenti, Modena (IT)

(73) Assignee: SOFAR SPA, Trezzano Rosa (IT)

(*) Notice: Subject to any disclaimer, the term of this patent is extended or adjusted under 35 U.S.C. 154(b) by 0 days.

(21) Appl. No.: 14/407,807

(22) PCT Filed: Jun. 13, 2013

(86) PCT No.: PCT/IB2013/054846
§ 371 (c)(1),
(2) Date: Dec. 12, 2014

(87) PCT Pub. No.: WO2013/186734
PCT Pub. Date: Dec. 19, 2013

(65) Prior Publication Data
US 2015/0164921 A1 Jun. 18, 2015

(30) Foreign Application Priority Data

Jun. 15, 2012 (IT) .............. MI2012A1041

(51) Int. Cl.
A61K 31/592 (2006.01)
A61K 31/593 (2006.01)
A61K 31/606 (2006.01)

(52) U.S. Cl.
CPC .......... A61K 31/606 (2013.01); A61K 31/592 (2013.01); A61K 31/593 (2013.01)

(58) Field of Classification Search
CPC ... A61K 31/592; A61K 31/593; A61K 31/606
See application file for complete search history.

(56) References Cited

U.S. PATENT DOCUMENTS

2001/0049364 A1 12/2001 Henrik
2010/0261174 A1 10/2010 Grande et al.

FOREIGN PATENT DOCUMENTS

| EP | 2239580 A1 | 10/2010 |
| WO | 9956697 A2 | 11/1999 |
| WO | 2006125073 A2 | 11/2006 |

OTHER PUBLICATIONS

PCT International Search Report and Written Opinion dated Aug. 27, 2013 for Intl. App. No. PCT/IB2013/054846, from which the instant application is based, 7 pgs.
Italian Search Report and Written Opinion dated Sep. 26, 2012 for related IT App. No. MI20121041, 7 pgs.
Bergman, R. et al., "Systematic review: the use of mesalazine in inflammatory bowel disease," Aliment Pharmacol & Ther. 2006, 23, pp. 841-855.
Bos, L. et al., "Protein phosphatase 2A is required for mesalazine-dependent inhibition of Wnt/β-catenin pathway activity," Carcinogenesis vol. 27, No. 12, 2006, pp. 2371-2382.
Guadagni, F. et al., "Non-steroidal Anti-inflammatory Drugs in Cancer Prevention and Therapy," AnticanCer Research 27: (2007), pp. 3147-3162.
Jimenez-Lara, A., "Colorectal cancer: Potential therapeutic benefits of Vitamin D," The Intl. Journal of Biochemistry & Cell Biology 39 (2007), pp. 672-677.
Livak, K. et al., "Analysis of Relative Gene Expression Data Using Real-Time Quantitative PCR and the 2-ΔΔCT Method," Methods, 25 (2001), pp. 402-408.
Losi, L. et al., "Down-regulation of μ-protocadherin expression is a common event in colorectal carcinogenesis," Human Pathology (2011) 42, pp. 960-971.
Luciani, M. Gloria et al, "5-ASA Affects Cell Cycle Progression in Colorectal Cells by Reversibly Activating a Replication Checkpoint," Gastroenterology 2007 132(1): 221-235.
Lyakhovich, A. et al., "Systematic review: molecular chemoprevention of colorectal malignancy by mesalazine," Alimentary Pharmacology & Therapeutics 31, 202-209.
O'Morain, C et al., "Concept of chemoprevention in colorectal cancer," World Journal of Gastrointestinal Oncology, 2009 V. 1, Issue 1, pp. 21-25.
Palmer, H. et al., "Vitamin D3 promotes the differentiation of colon carcinoma cells by the induction of E-cadherin and the inhibition of β-catenin signaling," The Journal of Cell Biology, vol. 154, 2001, pp. 369-387.
Parenti, S. et al., "Mesalazine inhibits the β-catenin signalling pathway acting through the upregulation of μ-protocadherin gene in colo-rectal cancer cells," Alimentary Pharmacology & Therapeutics 31, 108-119.
Reinacher-Schick, A. et al., "Mesalazine causes a mitotic arrest and induces caspase-dependent apoptosis in colon carcinoma cells," Carcinogenesis vol. 24, No. 3, 2003, pp. 443-451.
Rubin, D. et al., "Colorectal Cancer Prevention in Inflammatory Bowel Disease and the Role of 5-Aminosalicylic Acid: a Clinical Review and Update," Inflamm Bowel Dis vol. 14, No. 2, Feb. 2008, pp. 265-274.
Stolfi, C. et al., "Molecular basis of the potential of mesalazine to prevent colorectal cancer," World J Gasteroenterol Jul. 28, 2008, vol. 14, No. 28, pp. 4434-4439.
Tagliafico, E et al., "Identification of a molecular signature predictive of sensitivity to differentiation induction in acute myeloid leukemia," Leukemia (2006) 20, 1751-1758.

(Continued)

Primary Examiner — Zohreh A Fay
(74) Attorney, Agent, or Firm — Jeffrey N. Townes; Cozen O'Connor

(57) ABSTRACT

In the present invention, a new combination is disclosed comprising (i) 5-aminosalicylic acid (5-ASA) or a derivative thereof, or a pharmacologically acceptable salt thereof, and (ii) a group D vitamin, a derivative thereof, a metabolite or analogue, for use in the prevention and/or treatment of colorectal cancer (CRC). A further aspect of the invention is directed to pharmaceutical compositions comprising said combination together with at least one physiologically acceptable excipient and the use thereof in the prevention and/or in the treatment of the colorectal cancer.

10 Claims, 4 Drawing Sheets

(56) References Cited

OTHER PUBLICATIONS

Figure 1:
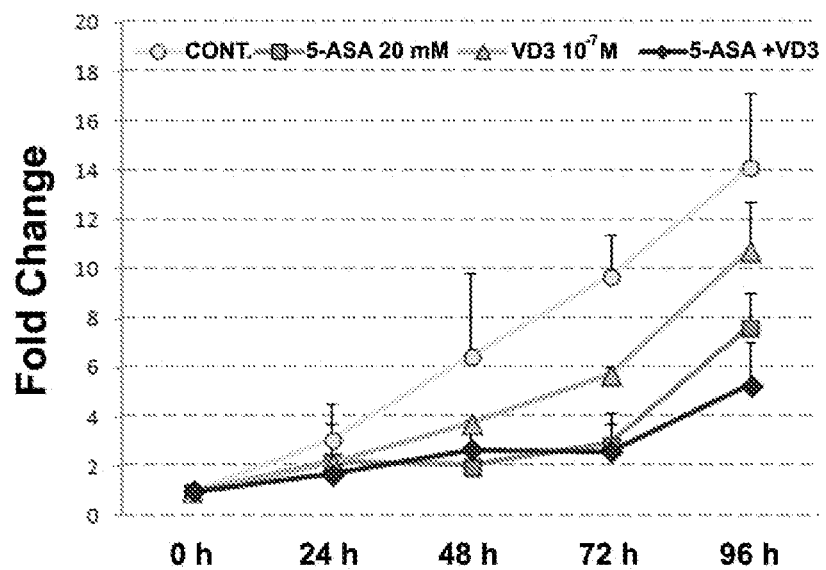

Christakos et al., "Vitamin D: Metabolism," Endocrinology & Metabolism Clinics of North America, vol. 39, No. 2, Jun. 2010, pp. 243-253.
DeLuca, "Overview of general physiologic features and functions of vitamin D," The American Journal of Clinical Nutrition, vol. 80, Dec. 2004, pp. 1689S-1696S.
Jones, "Vitamin D Analogs," Endocrinology & Metabolism Clinics of North America, vol. 39, No. 2, Jun. 2010, pp. 447-472.
Herszenyi et al., "Chemoprevention of colorectal cancer: feasibility in everyday practice?," European Journal of Cancer Prevention, vol. 17, No. 6, 2008, pp. 502-514.
Oh, Charles J. et al., "Treatment with anti-tumor necrosis factor $\alpha$ (TNF-$\alpha$) monoclonal antibody dramatically decreases the clinical activity of psoriasis lesions," J AM Acad Dermatol 42: 829-830 (2000).

CHEMOPREVENTION OF COLORECTAL CANCER

The present invention relates to a new combination of (i) 5-aminosalicylic acid (5-ASA) or a derivative thereof, or a pharmacologically acceptable salt thereof, and (ii) a group D vitamin, a derivative thereof, a metabolite or analogue, and to the use thereof in the prevention and/or treatment of colorectal cancer.

Another aspect of the invention relates to a pharmaceutical composition containing said combination together with at least one physiologically acceptable excipient and to said composition for use in the prevention and/or treatment of colorectal cancer.

PRIOR ART

Non Steroidal Anti-Inflammatory Drugs, NSAIDS, are characterised by a recognised chemopreventive activity against colorectal cancer (CRC) (O'Morain C et al., *World J Gastroenterol*, 2009; 1(1):21-15). Unfortunately, the systemic and gastrointestinal toxicity of NSAIDs drastically limits the administration thereof in the area of protocols that require long-term treatment of the patients concerned (Guadagni F. et al., *Anticancer Res*, 2007; 27:3147-3162). Different studies indicate that 5-ASA is a promising alternative for obtaining a comparable chemopreventive activity against CRC, at the same time avoiding the side effects induced by NSAIDs (Rubin D T et al., *Inflamm Bowel Dis*, 2008; 14:65-274). In fact, despite the chemical similarity with aspirin, i.e. a typical NSAID, 5-ASA is characterised by weak inhibition of cyclooxygenase, and by negligible systemic absorption, which are properties that clearly explain the clinical safety of this therapeutic agent (Bergman R. et al., *Aliment Pharmacol Ther*, 2006; 23:841-855). In this respect, it comes as no surprise that the anti-inflammatory effect of the 5-ASA is mediated by other mechanisms, amongst which an important role is probably played by the inhibition of transcription factors that promote the immune response, such as NFkB and the PPARs (Lyakhovich A. et al., *Aliment Pharmacol Ther*, 2010; 31(2):202-9).

Recent studies have then shown that the 5-ASA interferes with the proliferation signalling pathway mediated by the β-catenin. This protein is a transcription factor that is constitutionally activated in almost all cases of colorectal cancer. It is known that the state of phosphorylation of the β-catenin indirectly influences its transcription function, considering that this protein is degraded in the cytoplasm when it is phosphorylated whereas it is translocated to the nucleus when it is dephosphorylated. Bos et al., *Carcinogenesis* 2006; 27(12):2371-82 have demonstrated that 5-ASA is able to inhibit the enzyme activity of the phosphatase PP2A, normally responsible for dephosphorylation of the β-catenin, thus reducing the nuclear translocation thereof. Parenti S. et al., *Aliment Pharmacol Ther;* 31(1): 108-19 and Losi L. et al., *Hum Pathol* have also demonstrated that treating CRC cancer cells with 5-ASA induces the expression of a membrane protein, known as μ-protocadherin, which belongs to the superfamily of the cadherins and is able to sequester the β-catenin on the plasma membrane, preventing the β-catenin from translocating to the nucleus and activating the transcription of the target genes thereof.

EP2239580 has further demonstrated that the nuclear translocation of the β-catenin is inhibited after treatment with 5-ASA owing to the induction of a membrane protein belonging to the superfamily of the cadherins, said μ-protocadherin. This cadherin bonds and sequestrates in membrane the β-catenin, preventing the nuclear translocation thereof and the transcription of the target genes thereof.

Numerous epidemiological studies thereof suggest that also administering vitamin D3 (VD3) significantly reduces the occurrence of CRC. In addition to regulating calcium homeostasis, in fact, VD3 is also characterised by important antiproliferative, pro-differentiating and pro-apoptotic activity performed on numerous cell types amongst which it is also possible to cite cancer enterocytes of the colon (Jimenez-Lara A M., *Int J Biochem Cell Biol* 2007; 39(4):672-7). For this purpose, Palmer et al., *J Cell Biol* 2001; 154(2): 369-87 have demonstrated that VD3 interferes with the signal pathway of the β-catenin through a mechanism similar to that already mentioned for the 5-ASA that consists of a sequestration of this transcription factor on the plasma membrane that is in this case mediated by the hyperexpression of the E-cadherin or of the main epithelial cadherin.

DESCRIPTION OF THE INVENTION

The object of the present invention consists of finding new and more effective therapies for the treatment of colorectal cancer.

It was surprisingly found that the combination of (i) 5-aminosalicylic acid (5-ASA) or a derivative thereof, or a pharmacologically acceptable salt thereof, and (ii) a group D vitamin, a derivative thereof, a metabolite or analogue, enables both active principles to exert a synergic effect compared with the action of each single treatment on the transduction pathway of the proliferative signal of the β-catenin, the constitutive activation of which is observed in the progression of 90% of the colorectal cancers.

The present invention thus relates to a combination of (i) 5-aminosalicylic acid (5-ASA) or a derivative thereof, or a pharmacologically acceptable salt thereof, and (ii) a group D vitamin, a derivative thereof, a metabolite or analogue, and to a pharmaceutical composition comprising this combination in association with at least one physiologically acceptable excipient and to the use of said combination and/or pharmaceutical composition in the prevention and/or in the treatment of colorectal cancer.

The combination of the invention has the advantage of being able to reduce the therapeutic doses of both components with respect to the dosage that is usual in the prevention and/or in the treatment of colorectal cancer.

Preferably, the present invention relates to a combination of (i) 5-aminosalicylic acid (5-ASA) and (ii) a group D vitamin, a derivative thereof, a metabolite or analogue. The derivative of the 5-aminosalicylic acid (5-ASA) is preferably chosen from the group comprising sulfasalazine (acid 6-oxo-3-((4-(pyridin-2-yl)sulfamoyl]phenyl) hydrazinylidene]cyclohexa-1,4-diene-1-carboxylic), olsalazine (acid 5-[(2Z)-2-(3-carboxy-4-oxo-1-cyclohexa-2,5-dienilidene)hydrazinyl]-2-hydroxy-benzoic) and basalazide (acid 5-[4-(2-carboxyethylcarbamyl")phenyl]diazenyl-2-hydroxy-benzoic). Preferably, the group D vitamin, or a derivative thereof, metabolite or similar is chosen from the group comprising vitamin D3 (or cholecalciferol, IUPAC name: (3S,9S,10R,13R,14R,17R)-17-((2R,5R,E)-6-methylheptan-2-yl)-10,13-dimethyl-2,3,4,9,10,11,12,13,14,15,16,17-dodecahydro-1H-cyclopenta[α]phenanthren-3-ol), vitamin D2 (or ergocalciferol, IUPAC name: (3S,9S,10R,13R,14R, 17R)-17-((2R,5R,E)-5,6-dimethylheptan-3-en-2-yl)-10,13-dimethyl-2,3,4,9,10,11,12,13,14,15,16,17-dodecahydro-1H-cyclopenta[α]phenanthren-3-ol), 25-hydroxy-vitamin D3, (or calcifediol or calcidiol, IUPAC name: (6R)-6-[(1R,3aR, 4E,7aR)-4-[(2Z)-2-[(5S)-5-hydroxy-2-methylidene-cyclohexylidene]ethylidene]-7a methyl-2,3,3a,5,6,7-hexahydra-1H-inden-1-yl]-2-methyl-heptan-2-ol) and 1alpha,25 dihydroxy-vitamin D3 (or calcitriol, IUPAC name: (1R,3S)-5-[2-[(1R,3aR,7aS)-1-[(2R)-6-hydroxy-6-methylheptan-2-yl]-7a-methyl-2,3,3a,5,6,7-hexahydro-1H-inden-4-ylidene]ethylidene]-4-methylidene-cyclohexane-1,3-diol).

More preferably, the combination of the invention comprises vitamin D3.

According to one aspect of the present invention, said combination of 5-aminosalicylic acid (5-ASA) and vitamin D3 does not comprise calcium.

According to a further aspect of the present invention, said combination consists of 5-aminosalicylic acid (5-ASA) and vitamin D3.

According to one aspect, the present invention relates to a combination of 5-aminosalicylic acid (5-ASA) and vitamin D3, to a pharmaceutical composition comprising this combination in association with at least one physiologically acceptable excipient and to the use of said combination and/or pharmaceutical composition in the prevention and/or in the treatment of colorectal cancer.

According to another aspect, the present invention relates to the use of the combination and/or of the pharmaceutical composition of the present invention for preventing colorectal cancer in persons with a different risk of developing neoplasms, such as, for such example: healthy/normal individuals; patients affected by chronic inflammatory diseases of the intestine (such as Crohn's disease and ulcerous rectocolitis); patients subjected to endoscopic removal of adenomas and/or adenocarcinomas of the colon-rectum; patients affected by genetic cancer syndromes (like Lynch syndrome and familial adenomatous polyposis).

Suitable pathways for administering the combination and/or pharmaceutical composition of the invention include oral, intramuscular, subcutaneous or rectal administration, preferably oral administration.

The pharmaceutical composition of the present invention can be formulated as a combined preparation, for simultaneous, sequential or separate administration of the components of the combination, as pharmaceutical compositions in which the two components are present in the same dosage unit or in separate dosage units.

Preferably, separate administration of the two components occurs in an interval of time comprised between 1 and 24 hours.

The pharmaceutical composition of the present invention can be formulated in the form of tablets, capsules, granules, pills, lozenges.

According to a preferred aspect, the pharmaceutical composition of the present invention comprises the two components of the combination in association with at least one physiologically acceptable excipient in the same dosage unit in compressed form for oral administration.

The use of the combination of the invention for preventing and/or treating colorectal cancer involves daily administration of a quantity of 5-aminosalicylic acid (5-ASA) or a derivative thereof, or a pharmacologically acceptable salt thereof comprised in the range 0.5 to 5 g, preferably of about 2.4 g, and a quantity of a group D vitamin, a derivative thereof, a metabolite or analogue comprised in the range 500 to 10,000 IU, preferably about 2000 IU.

The quantity of composition of the invention to be administered to the patient can vary according to various factors that are well known to the skilled persons, for example, the weight of the patient, the administration pathway and the seriousness of the illness. According to a further aspect, the invention refers to a pharmaceutical composition that is suitable for the controlled release of the two components into distinct zones of the intestine, such as the small intestine for the group D vitamin, a derivative thereof, a metabolite or analogue, intended for systemic absorption in this place, and the colon for the 5-aminosalicylic acid (5-ASA) or a derivative thereof, or a pharmacologically acceptable salt thereof, where this compound has a topical effect, so that the corresponding concentrations of the two active components are optimum for the purposes of the object of the invention.

According to a preferred aspect, the combination and/or pharmaceutical composition of the present invention is administered to mammals, particularly to humans.

SHORT DESCRIPTION OF THE FIGURES

FIG. 1. Growth curve of the cell line HT29 subjected to treatment with 5-ASA, VD3 and 5-ASA+VD3. On the x axis treatment times are shown, on the y axis the number of cell expansions is shown compared with the initial number of cells. The data have been shown as averages±s.e.m obtained from three independent experiments.

Figure 2:
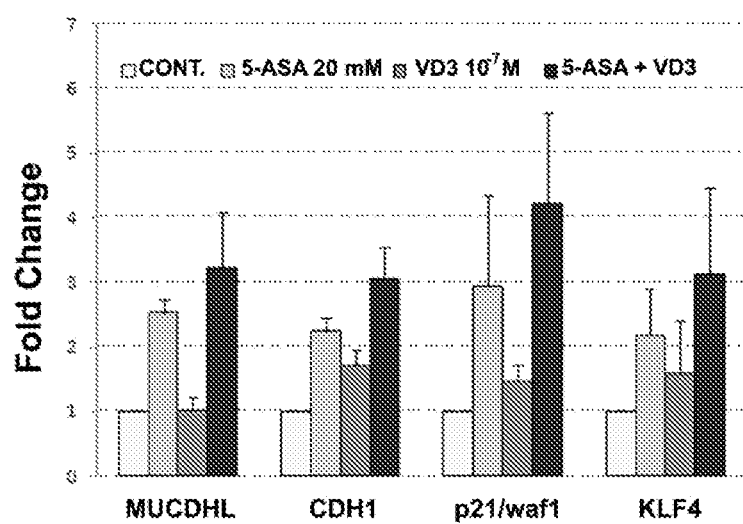

FIG. 2. QRT-PCR analysis of the RNA messengers of genes belonging to the signal pathway of the β chain in HT29 cells treated with 5-ASA, VD3 and 5-ASA+VD3. The analysed genes are shown on the x axis, whilst the quantitative variations of the levels of RNA messengers are shown on the y axis. The data have been displayed as averages±s.e.m obtained from three independent experiments.

Figure 3:
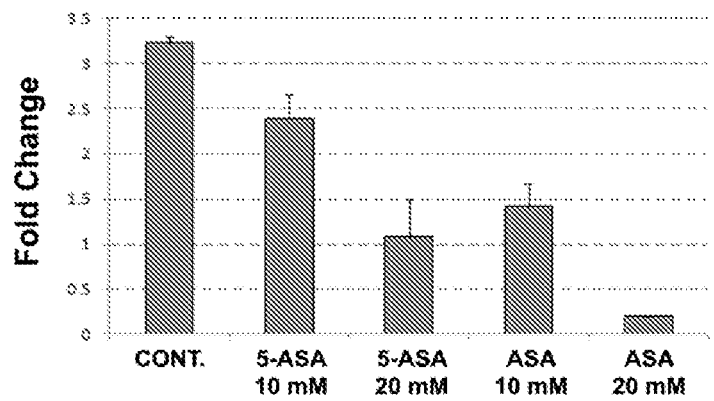

FIG. 3. Growth curve of the cell line CaCo2 subjected to treatment with 5-ASA and ASA. On the x axis, the analysed compounds and the concentrations thereof are shown, on the y axis, the number of cell expansions is shown compared with the initial number of cells. The data have been displayed as averages±s.e.m obtained from three independent experiments.

Figure 4:
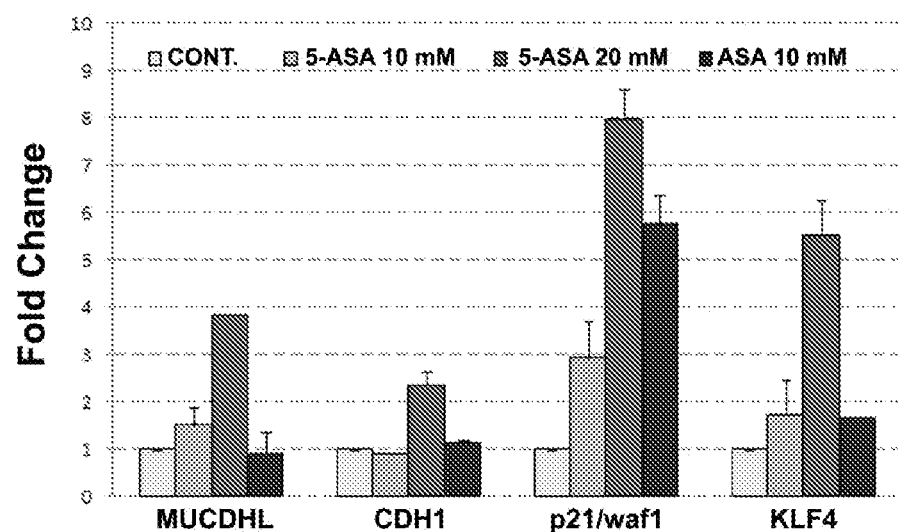

FIG. 4. QRT-PCR analysis of the RNA messengers of the genes belonging to the signal pathway of the β chain in CaCo2 cells treated with 5-ASA and ASA. The genes analysed are shown on the x axis, whereas the quantitative variations of the levels of RNA messenger are shown on the y axis. The data have been displayed as averages±s.e.m obtained from three independent experiments.

EXAMPLES

Material and Methods

The cell lines CaCo2 and HT29 of colorectal adenocarcinoma obtained from the ATCC (Rockville, Md., USA) were grown in a DMEM culture medium (Euroclone, Devon, UK), to which were added 10% foetal bovine serum (Lonza, Walkersville, Md., USA) inactivated at heat and 1 mM of L-glutamine (Euroclone). The 5-aminosalicylic acid (5-ASA, SOFAR S.p.A., Milan, Italy) and acetylsalicylic acid (ASA, Sigma Aldrich, St Louise, Mo., USA) were dissolved in a culture medium in a concentration of respectively 20 and 10 mM. The vitamin D3 (VD3) (1 alpha, 25 dihydroxyvitamin D3, calcitriol, Sigma Aldrich) was diluted in the culture medium at a concentration of $10^{-7}$ M. For the experiments conducted with the cell line HT29, 300,000 cells were sown for each sample and 5-ASA, vitamin D3 or the combination of 5-ASA and VD3 were added to each well. For the experiments conducted with the cell line CaCo2, on the other hand, 300,000 cells were again sown for each sample, but adding 5-ASA or ASA to each well. The treated cells were then subjected to a cell count every 24 hours to monitor the anti-proliferation effect of the different stimuli. After 96 hours of treatment all the cells were collected, resorbed and the RNA was extracted by means of the "Qiagen total RNA purification kit" following the manufacturer's instructions (Qiagen, Valencia, Calif.). The integrity and concentration of the RNA were tested using the Bio-Analyzer technique (Applied Biosystem, Foster City, Calif.). 100 ng total of RNA were then retrotranscribed using the High Capacity cDNA Archive Kit (Applied Biosystems) on the basis of the instructions provided by the manufacturer. The QRT-PCR was then carried out with an ABI PRISM 7900 (Applied Biosystems) sequence detecting system for quantifying the relative levels of mRNA measured in the various samples. The triggers and probes for amplifying the mRNA of the μ-protocadherin, E-cadherin, $p21^{waf-1}$, KLF4 and glyceraldehyde 3-phosphate dehydrogenase (GAPDH) were devised by Applied Biosystems. Each sample of cDNA was processed in triplicate in 50 μl of reaction volume using the Taqman Universal PCR Master Mix (Applied Biosystems). Thermal cyclisation was started with initial denaturation at 50° C. for 2 minutes and at 90° C. for 10 minutes followed by 40 cycles of 15 seconds at 95° C. and 1 minute at 60° C. The QRT-PCR signals were evacuated using the corresponding quantification method ΔΔCt (Livak K J, Schmittgen T D. Relative gene expression data were analysed using real-time quantitative PCR and the 2(-Delta Delta C(T)) Method. *Methods* 2001; 25(4):402-8). This procedure calculates the relative difference in gene expression of the target gene normalised on the endogen control (GAPDH) and compared with a calibrating sample. The values obtained were expressed as a relative quantity (RQ) of the variation in the messenger levels.

Example 1

Analysis of the Antiproliferal Effects Promoted by Treatment with 5-ASA and VD3 of the Adenocarcinoma Cell Line HT29 of the Colon-Rectum The colorectal adenocarcinoma cell line HT29, which was chosen for its responsiveness to the VD3 deriving from the corresponding VDR receptor, was subjected to "in vitro" treatment with 5-ASA 20 mM and VD3 $10^{-7}$ M, used individually and in association, in order to quantify the antiproliferative effect determined by the compounds analysed on cancerous colonocytes. The plotting of the growth curves, based on cell-count values obtained from this experiment, has shown that the treatment combined with 5-ASA and VD3 determines an additional antiproliferative effect that is clearly superior to what has been observed with the single treatments. This observation is evident above all at 96 hours of stimulation, where 14 expansions were detected in the control, 8 times in the treatment with 5-ASA, 10 times in the treatment with VD3 and only 5 times in the combined treatment (FIG. 1). These data confirm the antiproliferal effects achieved individually by treatment with 5-ASA and VD3 in colorectal cancer cells, further demonstrating the existence of an additional effect resulting from the pharmacological association thereof.

Example 2

QRT-PCR Analysis of Genes that Regulate Proliferation, Differentiation and Apoptosis in Colorectal Adenocarcinoma Cells HT29 of the Colon-Rectum Subjected to Treatment with 5-ASA and VD3

In order to check at the molecular level the effects determined on the cell line HT29 by the association 5-ASA/VD3, "Real Time", quantitative RT-PCR was used to analyse the expression of a series of genes the protein products of which are involved in the regulation of the proliferation, differentiation and apoptosis of cancer colonocytes such as μ-protocadherin, E-cadherin, $p21^{waf1}$ and KLF4. This analysis was conducted on cell cultures subjected to 96 hours of treatment with the studied drugs, which were used in the previously disclosed concentrations.

The choice of the listed genes derives from a series of observations explained below. μ-protocadherin and E-cadherin are proteins belonging to the family of the cadherins that mediate intercellular adhesion and therefore, indirectly, have an antimetastatic activity. It has also been demonstrated that they regulate cell proliferation by sequestering, on the plasma membrane, the transcription factor β-catenin and preventing it from activating the transcription of the target genes. For the reasons set out above, the expression of these cadherins is frequently down-regulated in epithelial tumours. The codifying gene for the protein $p21^{waf1}$ is one of the main negative targets of the β-catenin and is an important regulator of the cell cycle that is able to determine, following a massive induction of the expression thereof, proliferative arrest following cell death by apoptosis. Lastly, the KLF4 is a codifying oncosuppressor gene for a transcription factor that plays a crucial role in regulating the proliferation and differentiation of the colonocytes, partly deriving from the ability thereof to contrast the proliferative activity mediated by the β-catenin, or through molecular mechanisms that are only partially characterised. The importance of the genes mentioned so far is also fully underlined by the fact that they are all involved in the occurrence and progression of colorectal cancers.

The data obtained have demonstrated that single treatment with 5-ASA determines an increase in the messenger expression that is 2.5 times for the μ-protocadherin, 2.2 times for E-cadherin, 2.9 times for p21 and 2.2 times for KLF-4. After treatment with VD3, these values are respectively 1, 1.7, 1.5 and 1.6, whereas following combined treatment, they are respectively 3.2, 3.1, 4.2 and 3.1, showing that the association of the drugs in questions determines an additive effect on the induction of the messenger expression of the examined genes (FIG. 2).

These results clearly make the association 5-ASA/VD3 suitable for chemopreventive use against colorectal cancers.

Example 3

Comparative Analysis of the Antiproliferal and Molecular Effects Promoted by Treatment with 5-ASA and ASA in the Colorectal Adenocarcinoma Cell Line In order to characterise further the profile of efficacy and safety associated with the chemopreventive properties of 5-ASA, a series of experiments was conducted of the same type as the series explained previously, in which a comparative analysis was conducted of the biological effects determined on cancer colonocytes following treatment with 5-ASA and with aspirin (ASA), i.e. the main drug of the family of NSAIDs. These experiments were conducted in the colorectal adenocarcinoma cell line, owing to the elective responsive thereof to the 5-ASA emerging from the comparison with other cell lines of the same origin, exposing the culture to a treatment time of 96 hours.

The obtained results have demonstrated that although the ASA has a more pronounced antiproliferative effect than 5-ASA, this is associated with a clear toxic effect that is created at a concentration of 20 mM of the analysed drugs at which all the cells treated with 5-ASA survive, despite the complete proliferative block indicated by the cellularity "fold change" value equal to 1, whereas the cells subjected to treatment with ASA have 80% mortality, indicated by the cellularity "fold change" value equal to 0.2 (FIG. 3). An additional observation that arises from these results consists of the fact that a 10 mM concentration of ASA and 20 mM of 5-ASA can in fact be considered to be equivalents of the two compared drugs as they promote, on the cancer cells subjected to the treatment, an absolutely superimposable antiproliferative effect (FIG. 3).

On the samples taken from these cell cultures and from other cultures used as a control, the levels of messenger RNA of the genes listed in the previous paragraph (see FIG. 2) was determined by Quantitative Real Time RT-PCR. The obtained results have shown that the messenger expression of the μ-protocadherin, E-cadherin, $p21^{waf1}$ and KLF4 genes were induced respectively 3.8, 2.4, 8.0 and 5.5 times after treatment with 5-ASA 20 mM (FIG. 4), confirming the data previously observed on the cell line HT29. The treatment with the equivalent dose of ASA, equal to 10 mM, does not, on the other hand, induce any of the genes analysed with the sole exception of the gene $p21^{waf1}$ whose expression shows an increase of 5.8 times that thus appears to be comparable with what was observed in the corresponding treatment with 5-ASA. This datum is not surprising, considering the redundancy and heterogeneity that characterise molecular regulation of the gene $p21^{waf1}$, the expression of which is not only regulated by the proliferation signalling pathway of the β chain, explored in our experimental conditions through the evaluation of the codifying genes for μ-protocadherin, E-cadherin and KLF4, but also by numerous signalling pathways. The most plausible conclusion arising from this result consequently consists of the consideration that the ASA induces the expression of the $p21^{waf1}$ through molecular mechanisms that are other than those that mediate the same effect through 5-ASA, thus demonstrating a specificity of action of the latter in relation to the compared drug.

Overall, the data presented so far thus indicate that: 1) 5-ASA inhibits the signal pathway of the β-catenin and, consistently, the proliferative activity of cancer colonocytes, working in cooperation with the VD3, which makes this pharmacological association suitable for chemiopreventive use against colorectal cancer; 2) the 5-ASA is less toxic and thus safer than the ASA for the purposes of prolonged use such as that required for the purposes of obtaining chemiopreventive protection; 3) equivalent doses of ASA and 5-ASA act through distinct molecular mechanisms, which vindicates the specificity of action of the 5-ASA compared with the ASA.

BIBLIOGRAPHY

1. Reinacher-Schick A, Schoeneck A, Graeven U, Schwarte-Waldhoff I, Schmiegel W. Mesalazine causes a mitotic arrest and induces caspase-dependent apoptosis in colon carcinoma cells. *Carcinogenesis* 2003; 24(3):443-51.
2. Luciani M G, Campregher C, Fortune J M, Kunkel T A, Gasche C. 5-ASA affects cell cycle progression in colorectal cells by reversibly activating a replication checkpoint. *Gastroenterology* 2007; 132(1):221-35.
3. Stolfi C, Pellegrini R, Franze E, Pallone F, Monteleone G. Molecular basis of the potential of mesalazine to prevent colorectal cancer. *World J Gastroenterol* 2008; 14(28): 4434-9.
4. Lyakhovich A, Gasche C. Systematic review: molecular chemoprevention of colorectal malignancy by mesalazine. *Aliment Pharmacol Ther;* 31(2):202-9.
5. Bos C L, Diks S H, Hardwick J C, Walburg K V, Peppelenbosch M P, Richel D J. Protein phosphatase 2A is required for mesalazine-dependent inhibition of Wnt/beta-catenin pathway activity. *Carcinogenesis* 2006; 27(12):2371-82.
6. Parenti S, Ferrarini F, Zini R, Montanari M, Losi L, Canovi B, et al. Mesalazine inhibits the beta-catenin signalling pathway acting through the upregulation of mu-protocadherin gene in colo-rectal cancer cells. *Aliment Pharmacol Ther;* 31(1):108-19.
7. Losi L, Parenti S, Ferrarini F, Rivasi F, Gavioli M, Natalini G, et al. Down-regulation of mu-protocadherin expression is a common event in colorectal carcinogenesis. Hum Pathol.
8. Grande A P, S. Ferrarini, F., inventor Determination of 5-ASA efficacy in CRC prevention and/or treatment by gene expression analysis. 2009.
9. Tagliafico E, Tenedini E, Manfredini R, Grande A, Ferrari F, Roncaglia E, et al. Identification of a molecular signature predictive of sensitivity to differentiation induction in acute myeloid leukemia. *Leukemia* 2006; 20(10):1751-8.
10. Jimenez-Lara A M. Colorectal cancer: potential therapeutic benefits of Vitamin. D. *Int J Biochem Cell Biol* 2007; 39(4):672-7.
11. Palmer H G, Gonzalez-Sancho J M, Espada J, Berciano M T, Puig I, Baulida J, et al. Vitamin D(3) promotes the differentiation of colon carcinoma cells by the induction of E-cadherin and the inhibition of beta-catenin signaling. *J Cell Biol* 2001; 154(2):369-87.
12. Livak K J, Schmittgen T D. Analysis of relative gene expression data using real-time quantitative PCR and the 2(-Delta Delta C(T)) Method. *Methods* 2001; 25(4):402-8.

The invention claimed is:
1. A combination, comprising:
   (i) a 5-aminosalicylic acid component, wherein the 5-aminosalicylic acid component comprises 5-aminosalicylic acid or a pharmacologically acceptable salt of 5-aminosalicylic acid; and
   (ii) a group D vitamin component, wherein the group D vitamin component is selected from the group consisting of vitamin D3, vitamin D2, 25-hydroxy-vitamin D3 and 1-alpha,25 dihydroxy-vitamin D3;
   wherein the combination includes between 0.5 grams and 5 grams of the 5-aminosalicylic acid component and between 500 international units and 10,000 international units of the group D vitamin component; and
   wherein the combination does not include calcium.
2. The combination of claim 1 wherein the combination comprises 5-aminosalicylic acid and vitamin D3.
3. The combination of claim 1 wherein the combination consists of 5-aminosalicylic acid and vitamin D3.

4. The combination of claim 1 wherein the combination is part of a pharmaceutical composition comprising the combination together with at least one physiologically acceptable excipient.

5. The combination of claim 4 wherein the pharmaceutical composition is a tablet, capsule, granule, pill, or lozenge.

6. The combination of claim 4 wherein the pharmaceutical composition is suitable for controlled release of the 5-aminosalicylic acid component and the group D vitamin component.

7. The combination of claim 4 wherein the pharmaceutical composition is provided as a combined preparation, wherein the combined preparation allows for simultaneous, sequential or separate administration of the 5-aminosalicylic acid component and the group D vitamin component.

8. The combination of claim 1 wherein the combination comprises 5-aminosalicylic acid and vitamin D2.

9. The combination of claim 1 wherein the combination comprises 5-aminosalicylic acid and 25-hydroxy-vitamin D3.

10. The combination of claim 1 wherein the combination comprises 5-aminosalicylic acid and 1-alpha,25 dihydroxy-vitamin D3.

\* \* \* \* \*